United States Patent [19]
Winter et al.

[11] Patent Number: 6,063,880
[45] Date of Patent: *May 16, 2000

[54] PROCESS FOR THE PREPARATION OF A POLYOLEFIN WAX

[75] Inventors: Andreas Winter, Kelkheim/Taunus; Jürgen Rohrmann, Liederbach; Volker Dolle, Kelkheim/Taunus; Martin Antberg, Hofheim am Taunus; Walter Spaleck, Liederbach, all of Germany

[73] Assignee: Targor GmbH, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/464,458

[22] Filed: Jun. 5, 1995

Related U.S. Application Data

[62] Division of application No. 08/287,101, Aug. 8, 1994, abandoned, which is a continuation of application No. 07/577,899, Sep. 5, 1990, abandoned.

[30] Foreign Application Priority Data

Sep. 7, 1989 [DE] Germany .............................. 39 29 693

[51] Int. Cl.⁷ .................................................... C08F 4/642
[52] U.S. Cl. ............................ 526/160; 526/127; 585/10; 585/18; 585/512; 585/946
[58] Field of Search .................................... 526/127, 150, 526/160; 585/10, 18, 512, 946

[56] References Cited

U.S. PATENT DOCUMENTS

| | | | |
|---|---|---|---|
| 4,962,248 | 10/1990 | Winter et al. .............................. | 585/12 |
| 4,962,262 | 10/1990 | Winter et al. .............................. | 585/512 |
| 5,023,388 | 6/1991 | Luker ............................................ | 585/9 |
| 5,416,178 | 5/1995 | Winter et al. .............................. | 526/160 |

FOREIGN PATENT DOCUMENTS

| | | |
|---|---|---|
| 0 321 851 | 5/1989 | European Pat. Off. . |
| 0 321 852 | 6/1989 | European Pat. Off. . |
| 0 321 853 | 6/1989 | European Pat. Off. . |
| 31 48 229 | 6/1983 | Germany . |
| 37 26 067 | 2/1989 | Germany . |
| 37 43 321 | 6/1989 | Germany . |
| 3743321 | 6/1989 | Germany . |
| 59-206409 | 11/1984 | Japan . |
| 62-129303 | 6/1987 | Japan . |

OTHER PUBLICATIONS

Kaminsky et al., Makromol. Chem. Makromol. Symp. 3, pp. 377–387 (1986).
Kaminsky et al., *Angew Chem.*, 97: pp. 507–508 (1985) Nr. 6.
English Translation Furnished.
Kaminsky et al (1987), Macromal. Chem. Macromal. Symp. 3, 377–387 (1986).

*Primary Examiner*—Fred Teskin
*Attorney, Agent, or Firm*—Connolly Bove Lodge & Hutz LLP

[57] ABSTRACT

If a catalyst consisting of an aluminoxane and a metallocene of the formula I

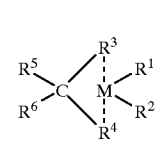

(I)

in particular $R^5R^6C$ $(Ind)_2$ or $R^5R^6C$ $(Ind)_2$ $Zr(CH_3)_2$, is employed for the polymerization of olefins of the formula $$R^9CH=CHR^{10}$$

($R^9$, $R^{10}$=H or $C_1$–$C_{28}$ alkyl), the isotacticity of the polymer wax and hence the hardness and melting point can be varied simply by changing the polymerization temperature, without the molecular weight of the polymer being noticeably changed at the same time.

25 Claims, No Drawings

PROCESS FOR THE PREPARATION OF A POLYOLEFIN WAX

This application is a divisional of application Ser. No. 08/287,101 filed Aug. 8, 1994 now abandoned which is a continuation of Ser. No. 07/577,899 filed Sep. 5, 1990 now abandoned.

The invention relates to a process for the preparation of a polyolefin wax, it being possible for the tacticity of the polymer chains to be modified by the choice of polymerization temperature without the viscosity number of the polymer being changed.

The preparation of isotactic polyolefin waxes (isotacticity index 80 to 85%, fusion enthalpy 63 J/g, mixtures of atactic and isotactic polyolefin chains) by means of a supported catalyst, cocatalyst and stereoregulator at temperatures of more than 95° C. is known (DE-A-3,148,229). Large amounts of nydrogen have to be employed as a molecular weight regulator.

An $MgCl_2$ supported contact catalyst which leads to crystalline PP waxes having a narrow molecular weight distribution is furthermore also known (Japanese Patent 59/206,409). This catalyst also has the disadvantages typical of catalyst systems which have been developed for the preparation of high molecular weight polyolefins and thus have a low activity in the preparation of low molecular weight polyolefins. An undesirable mixture of isotactic and atactic chains is furthermore also present here in the wax product.

Waxy random ethylene copolymers having a 1-olefin content of 1 to 15 mol %, which are prepared using a catalyst system based on zirconium hydride-metallocene/aluminoxane, are furthermore known (Japanese Patent 62/129,303). However, such metallocenes are not suitable for producing isotactic polypropylene; their activity in the polymerization of propylene is moreover very low.

As a result of the low catalyst activities under the reaction conditions required, relatively high chlorine contents of in some cases more than 1,000 ppm are found in the polymer waxes if the catalyst residues are not removed by an expensive specific after-treatment.

The use of metallocene/aluminoxane/hydrogen catalyst systems for the preparation of highly isotactic 1-olefin polymer waxes has also been proposed (German Patent 3,743,321).

It has been possible to overcome the disadvantages of the processes described above using this catalyst, but the high isotacticity of the products has led to extremely hard waxes, which is undesirable for a number of uses of the waxes.

Concomitant phenomena of the high isotacticity achieved by this process are melting points which are too high for many uses of the waxes. Hydrogen is furthermore used to adjust the molecular weight, and a process which could dispense with the use of a molecular weight regulator would lead to a significant simplification of the process.

One main possibility for reducing the hardness is subsequent admixing of atactic poly-1-olefin wax. Apart from the uneconomically high costs which are unacceptable on a large industrial scale, this admixing leads to non-uniform and tacky products.

It is known from the literature that a lower molecular weight polymer is formed with metallocene/aluminoxane systems at a high polymerization temperature than at lower temperatures (W. Kaminsky et al., macromol. Chem., Macromol. Symp., 3 (1986) 377) and at the same time the tacticity of the polymer chains is changed here only slightly (W. Kaminsky et al., Angew. Chem. 97 (1985) 507).

There was thus the object of discovering a process with which polyolefin waxes of different isotacticity but comparable molecular weight and narrow molecular weight distribution can be prepared.

It has been found that the object can be achieved if a specifically bridged metallocene is used.

The invention thus relates to a process for the preparation of a polyolefin wax by polymerization or copolymerization of an olefin of the formula $R^9CH=CHR^{10}$, in which $R^9$ and $R^{10}$ are identical or different and are a hydrogen atom or an alkyl radical having 1 to 28 carbon atoms, or $R^9$ and $R^{10}$, together with the atoms joining them, can form a ring, at a temperature of −60 to 200° C. under a pressure of 0.5 to 100 bar, in solution, in suspension or in the gas phase, in the presence of a catalyst which consists of a metallocene and an aluminoxane of the formula II

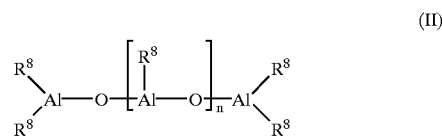

(II)

for the linear type, and/or of the formula III

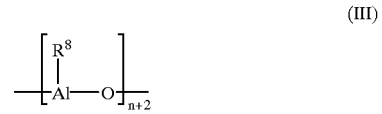

(III)

for the cyclic type, in which, in the formulae II and III, $R^8$ is a $C_1$–$C_6$-alkyl group or a $C_6$–$C_{10}$-aryl group and n is an integer from 2 to 50, wherein the metallocene is a compound of the formula I

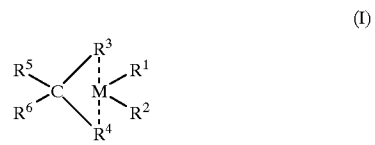

(I)

in which M is a metal of group IVb, Vb or VIb of the periodic table, $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom, $R^3$ and $R^4$ are identical or different and are a mono- or polynuclear hydrocarbon radical which can form a sandwich structure with the transition metal, and $R^5$ and $R^6$ are identical or different and are a hydrogen atom, a halogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a —$SiR_3^7$, —$NR_2^7$, —$PR_2^7$, —$P(O)R_2^7$, —$Si(OR^7)R_2^7$, —$Si(OR^7)_2R^7$, —$Si(OR^7)_3$, —$AsR_2^7$ or —$SR^7$ radical, in which $R^7$ has the meaning of $R^1$.

The invention furthermore relates to the polyolefin wax prepared by this process.

The catalyst to be used for the process according to the invention consists of an aluminoxane and a metallocene of the formula I

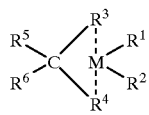

(I)

M is a metal of group IVb, Vb or VIb of the periodic table, preferably Ti, Zr or Hf, particularly preferably Zr.

$R^1$ and $R^2$ are identical or different and are a hydrogen atom, a $C_1$–$C_{10}$-, preferably $C_1$–$C_3$-alkyl group, a $C_1$–$C_{10}$-, preferably $C_1$–$C_3$-alkoxy group, a $C_6$–$C_{10}$-, preferably $C_6$–$C_8$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{10}$-arylalkyl group, a $C_7$–$C_{40}$-, preferably $C_7$–$C_{12}$-alkylaryl group, a $C_8$–$C_{40}$-, preferably $C_8$–$C_{12}$-arylalkenyl group or a halogen atom, preferably chlorine.

$R^3$ and $R^4$ are identical or different, preferably identical, and are a mono- or polynuclear hydrocarbon radical which can form a sandwich structure with the transition metal, substituted cyclopentadienyl radicals being preferred. The indenyl radical is particularly preferred.

$R^5$ and $R^6$ are identical or different and are a hydrogen atom, a halogen atom, a $C_1$–$C_{10}$-, preferably $C_1$–$C_3$-alkyl group, a $C_1$–$C_{10}$-, preferably $C_1$–$C_3$-alkoxy group, a $C_6$–$C_{10}$-, preferably $C_6$–$C_8$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{10}$-arylalkyl group, a $C_7$–$C_{40}$-, preferably $C_7$–$C_{12}$-alkylaryl group, a $C_8$–$C_{40}$-, preferably $C_8$–$C_{12}$-arylalkenyl group or a —$SiR_3^7$, —$NR_2^7$, —$PR_2^7$, —$P(O)R_2^7$, —$Si(OR)R_2^7$, —$Si(OR^7)_2R^7$, —$Si(OR^7)_3$, —$AsR_2^7$ or —$SR^7$ radical, in which $R^7$ has the meaning given for $R^1$.

Alkyl and aryl groups are preferred.

Preferred metallocene compounds are $R^5R^6C$(bisindenyl)$ZrCl_2$ and $R^5R^6C$(bisindenyl)$Zr(CH_3)_2$.

$Ph_2C$(bisindenyl)$ZrCl_2$ and $(CH_3)_2C$(bisindenyl)$ZrCl_2$ are particularly preferred.

The metallocenes described above can be prepared in accordance with the following general equation:

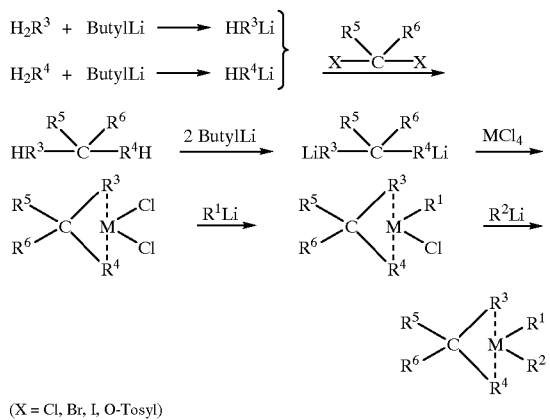

(X = Cl, Br, I, O-Tosyl)

or:

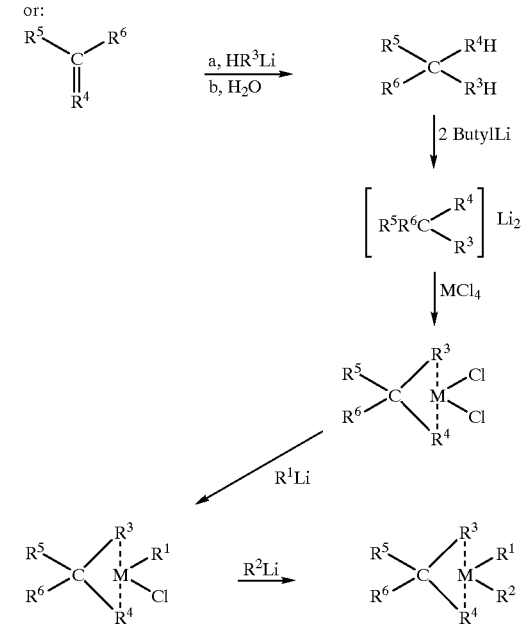

The cocatalyst is an aluminoxane of the formula II

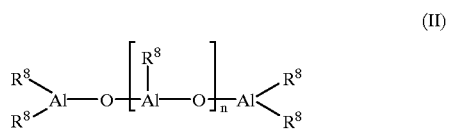

(II)

for the linear type, and/or of the formula III

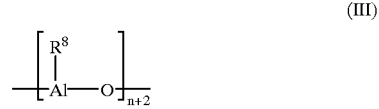

(III)

for the cyclic type. In these formulae, $R^8$ is a $C_1$–$C_6$-alkyl group, preferably methyl, ethyl or isobutyl, butyl or neopentyl, or a $C_6$–$C_{10}$-aryl group, preferably phenyl or benzyl. Methyl is particularly preferred. n is an integer from 2 to 50, preferably 5 to 40. However, the exact structure of the aluminoxane is not known.

The aluminoxane can be prepared in various ways.

One possibility is careful addition of water to a dilute solution of an aluminum trialkyl by introducing the solution of the aluminum trialkyl, preferably aluminum trimethyl, and the water, each in small portions, into a relatively large amount of an inert solvent which has been initially introduced into the reaction vessel, and in each case awaiting the end of the evolution of gas between the additions.

In another process, finely powdered copper sulfate pentahydrate is suspended in toluene in a glass flask and aluminum trialkyl is added under an inert gas at about −20° C. in an amount such that about 1 mol of $CuSO_4 \cdot 5H_2O$ is available for each 4 Al atoms. After slow hydrolysis, alkane being split off, the reaction mixture is left at room temperature for 24 to 48 hours, during which it must be cooled, if appropriate, so that the temperature does not rise above 30° C. The copper sulfate is then filtered off from the aluminoxane dissolved in the toluene and the solution is concentrated in vacuo. It is assumed that during this preparation process the low molecular weight aluminoxanes undergo condensation to higher oligomers, aluminum trialkyl being split off.

Aluminoxanes are furthermore obtained if aluminum trialkyl, preferably aluminum trimethyl, dissolved in an inert aliphatic or aromatic solvent, preferably heptane or toluene, is reacted with aluminum salts containing water of crystallization, preferably aluminum sulfate, at a temperature of −20 to 100° C. In this procedure, the volume ratio between the solvent and the aluminum trialkyl used is 1:1 to 50:1— preferably 5:1— and the reaction time, which can be monitored by the splitting off of the alkane, is 1 to 200 hours—preferably 10 to 40 hours.

Of the aluminum salts which contain water of crystallization, those which have a high content of water of crystallization are used in particular. The particularly preferred salt is aluminum sulfate hydrate, especially the compounds $Al_2(SO_4)_3 \cdot 16H_2O$ and $Al_2(SO_4)_3 \cdot 18H_2O$ having the particularly high water of crystallization content of 16 and 18 mol of $H_2O$/mol of $Al_2(SO_4)_3$ respectively.

Another variant for the preparation of aluminoxanes comprises dissolving aluminum trialkyl, preferably aluminum trimethyl, in the suspending agent initially introduced into the polymerization system, preferably in the liquid monomer, in heptane or toluene, and then reacting the aluminum compound with water.

In addition to the processes described above for the preparation of aluminoxanes, there are others which can be used. A varying content of unreacted aluminum trialkyl, which is present in the free form or as an adduct, is a common feature of all aluminoxane solutions, regardless of the nature of their preparation. This content has an influence which has not yet been accurately explained on the catalytic activity and which varies according to the metallocene compound employed.

It is possible for the metallocene to be preactivated with an aluminoxane of the formula II and/or III before being used in the polymerization reaction. The polymerization activity is in this way increased significantly and the particle morphology improved.

The preactivation of the transition metal compound is carried out in solution. Preferably, in this procedure, the metallocene is dissolved in a solution of the aluminoxane in an inert hydrocarbon. A suitable inert hydrocarbon is an aliphatic or aromatic hydrocarbon. Toluene is preferably used.

The concentration of the aluminoxane in the solution is in the range from about 1% by weight up to the saturation limit, preferably 5 to 30% by weight, in each case based on the total solution. The metallocene can be employed in the same concentration, but it is preferably employed in an amount of $10^{-4}$—1 mol per mol of aluminoxane. The preactivation time is 5 minutes to 60 hours, preferably 5 to 60 minutes. The preactivation is carried out at a temperature of −78° C. to 100° C., preferably 0 to 70° C.

A significantly longer preactivation is possible, but normally neither increases the activity nor reduces the activity, although it may be entirely appropriate for storage purposes.

The polymerization is carried out in a known manner in solution, in suspension or in the gas phase, continuously or discontinuously, in one or more stages, at a temperature of −60 to 200° C., preferably −30 to 100° C., in particular 0 to 80° C.

The total pressure in the polymerization system is 0.5 to 100 bar. Polymerization in the pressure range of 5 to 60 bar, which is of particular industrial interest, is preferred. Monomers having a boiling point higher than the polymerization temperature are preferably polymerized under normal pressure.

The metallocene compound is used in this process in a concentration, based on the transition metal, of $10^{-3}$ to $10^{-8}$, preferably $10^{-4}$ to $10^{-7}$ mol of transition metal per $dm^3$ of solvent or per $dm^3$ of reactor volume. The aluminoxane is used in a concentration of $10^{-5}$ to $10^{-1}$ mol, preferably $10^{-5}$ to $10^{-2}$ mol per $dm^3$ of solvent or per $dm^3$ of reactor volume. On principle, however, higher concentrations are also possible.

If the polymerization is carried out as suspension or solution polymerization, an inert solvent which is customary for the Ziegler low pressure process is used. For example, the polymerization is carried out in an aliphatic or cycloaliphatic hydrocarbon; butane, pentane, hexane, heptane, isooctane, cyclohexane and methylcyclohexane may be mentioned as examples thereof.

A benzine or hydrogenated diesel oil fraction can furthermore be used. Toluene can also be used. The polymerization is preferably carried out in the liquid monomer.

Olefins of the formula $R^9CH{=}CHR^{10}$, in which $R^9$ and $R^{10}$ are identical or different and are a hydrogen atom or an alkyl radical having 1 to 28 carbon atoms, it also being possible for $R^9$ and $R^{10}$ to form a ring with the carbon atoms joining them, are polymerized or copolymerized. Examples of such olefins are ethylene, propylene, 1-butene, 1-hexene, 4-methyl-1-pentene, 1-octene, norbornene and norbornadiene. Propylene is preferred.

The polymerization can be of any desired duration, since the catalyst system to be used according to the invention shows only a slight drop in the polymerization activity as a function of time.

The process according to the invention is distinguished by the fact that the molecular weight of the polymers prepared is practically unchanged in the temperature range between 30 and 80° C., which is of interest industrially, but that the isotacticity of the polymer chains can be varied between about 98 and 50% ($^{13}$C-NMR data) by varying the temperature.

The hardness and melting point can in this way be adjusted in a controlled manner without a change in the viscosity number of the polymer, and a tailor-made product can therefore be produced. The polymer powders prepared are distinguished by an excellent powder morphology—good flow properties and high bulk density.

The use of hydrogen can furthermore be dispensed with, which additionally results in the possibility of functionalization of the polyolefin waxes due to the formation of unsaturated chain ends (β-elimination mechanism). Dispensing with hydrogen means a significant simplification of the process.

The following example s are intended to illustrate the invention. In these examples:

VN=viscosity number in $cm^3/g$ $M_w$=weight-average molecular weight in g/mol $M_n$=number-average molecular weight in g/mol $M_w/M_n$=molecular weight distribution The molecular weights were determined by gel permeation chromatography.

$^{13}$C-NMR spectroscopy:

II=isotactic index $n_{iso}$=average isotactic block length $$\left(1 + \frac{2mm}{mr}\right)$$

BD=polymer bulk density in $g/dm^3$

MV=melt viscosity, determined by means of a rotary viscometer at 170° C.

M.P.=melting point, determined by differential scanning calorimetry measurement (20° C./minute heating up/cooling down rate); the heat of fusion was also determined by means of differential scanning calorimetry.

The metallocene and aluminoxane were handled under an inert gas.

EXAMPLE 1

2,2-Bis-(1-indenyl)propane 18.8 cm$^3$ (47.0 mmol) of n-butyllithium were added at 0° C. to a solution of 5.93 g (47.0 mmol) of indene (industrial, 91% pure) filtered over Al$_2$O$_3$. After the mixture had been stirred at room temperature for 15 minutes, the solution was slowly added dropwise to a solution of 7.40 g (47.0 mmol) of 1-isopropylideneindene. After the mixture had been stirred at room temperature for 2 hours, 50 cm$^3$ of water were added and the mixture was extracted with diethyl ether. The yellow organic phase was dried over MgSO$_4$. The residue which remained after the solvent had been stripped off was chromatographed on silica gel 60. 1.5 g (13%) of the product (2 isomers) could be isolated with hexane/methylene chloride (10:1).

Racemic isopropylidene-bis-(1-indenyl)-zirconiumdichloride 5.30 cm$^3$ (13.0 mmol) of n-butyllithium (2.5 M/hexane) were added to a solution of 1.50 g (5.51 mmol) of 2,2-bis-(1-indenyl)propane in 15 cm$^3$ of diethyl ether, while cooling with water. After the mixture had been stirred at room temperature for 2 hours, 10 cm$^3$ of hexane were added. The colorless precipitate was filtered off over a glass frit, washed with hexane and dried under an oil pump vacuum. 1.96 g of the dilithium salt, which still contained about 20% by weight of diethyl ether, were obtained (quantitative yield). This salt was added to a suspension of 1.28 g (5.51 mmol) of ZrCl$_4$ in 25 cm$^3$ of methylene chloride at –78° C. The reaction mixture was slowly warmed to room temperature in the course of about 6 hours. The orange precipitate was filtered off over a glass frit, washed with a little methylene chloride and dried under an oil pump vacuum. 930 mg (39%) of the complex racemic ((CH$_3$)$_2$C(1-indenyl)$_2$)ZrCl$_2$ were obtained as an orange-colored crystalline powder. Correct mass spectrum (M$^+$=432).

$^1$H-NMR spectrum (CDCl$_3$): 6.92–7.80 (m, 8, aromatic H), 6.70 (dd, 2, β-IndH), 6.15 (d, 2, α-IndH), 2.37 (s, 6, CH$_3$).

EXAMPLE 2

A dry 16 dm$^3$ reactor was flushed with nitrogen and filled with 10 dm$^3$ of liquid propylene. 30 cm$^3$ of a toluene solution of methylaluminoxane (corresponding to 40 mmol of Al, average degree of oligomerization of the methylaluminoxane n=20) were then added and the mixture was stirred at 30° C. for 15 minutes. In parallel with this, 105 g (0.243 mmol) of racemic isopropylidene-bis-(1-indenyl)-zirconium dichloride were dissolved in 15 cm$^3$ of a toluene solution of methylaluminoxane (20 mmol of Al) and preactivated by being left to stand for 15 minutes. The violet solution was then introduced into the kettle. The polymerization was carried out at 30° C. for 5 hours. 3.10 kg of polypropylene wax were obtained, corresponding to a metallocene activity of 5.9 kg of PP/g of metallocene×h.

VN=14.0 cm$^3$/g; M$_w$=15,900, M$_n$=6,500, M$_w$/M$_n$=2.4; II=95.6%, n$_{iso}$=36, BD=360 g/dm$^3$; MV=470 mPa.s; M.P.= 142° C., heat of fusion=105 J/g; ball indentation hardness= 1,400 bar, drawing hardness=>1,000 bar.

EXAMPLE 3

The procedure was as in Example 1, but 78.3 mg (0.181 mmol) of the metallocene were used, the polymerization temperature was 40° C. and the polymerization time was 3 hours.

2.32 kg of propylene wax were obtained, corresponding to a metallocene activity of 9.9 kg of PP/g of metallocene×h.

VN=14.7 cm$^3$/g; M$_w$=6,500, M$_n$=5,800, M$_w$/M$_n$=2.8; II=90.2%, n$_{iso}$=21; BD=382 g/dm$^3$; MV=490 mPa.s; M.P.= 132° C., heat of fusion=80 J/g; ball indentation hardness= 1,170 bar, drawing hardness=>1,000.

EXAMPLE 4

The procedure was as in Example 1, but 28.9 mg (0.067 mmol) of the metallocene were used, the polymerization temperature was 60° C. and the polymerization time was 2 hours.

2.38 kg of polypropylene wax were obtained, corresponding to a metallocene activity of 41.2 kg of PP/g of metallocene×h.

VN=13.5 cm$^3$/g; M$_w$=14,150, M$_n$=5,300, M$_w$/M$_n$=2.6; II=85.8%, n$_{iso}$=14; BD=415 g/dm$^3$; MV=390 mpa.s; M.P.= 125° C., heat of fusion=72 J/g; ball indentation hardness= 762 bar, drawing hardness=1,000 bar.

EXAMPLE 5

The procedure was as in Example 1, but 37.3 mg (0.086 mmol) of the metallocene were used, the polymerization temperature was 70° C. and the polymerization time was 1 hour.

2.36 kg of polypropylene wax were obtained, corresponding to a metallocene activity of 63.3 kg of PP/g of metallocene×hour.

VN=13.6 cm$^3$/g; M$_w$=14,750, M$_n$=5,050, M$_w$/M$_n$=2.9; II=79.7%, n$_{iso}$=11.5; BD=362 g/dm$^3$; MV=450 mPa.s; M.P.=124° C., heat of fusion=65 J/g; ball indentation hardness=254 bar, drawing hardness=780 bar.

EXAMPLE 6

The procedure was as in Example 1, but 15.0 mg (0.035 mol) of the metallocene were used, the polymerization temperature was 78° C. and the polymerization time was 1 hour.

1.58 kg of polypropylene wax were obtained, corresponding to a metallocene activity of 105.3 kg of PP/g of metallocene×hour.

VN=13.5 cm$^3$/g; M$_w$=14,200, M$_n$=5,600, M$_w$/M$_n$=2.5; II=70.5%, n$_{iso}$=9; BD=380 g/dm$^3$; M.P.=120° C., heat of fusion=59 J/g.

We claim:

1. A process for the preparation of a polyolefin wax by polymerization or copolymerization of an olefin of the formula R$^9$CH=CHR$^{10}$, in which R$^9$ and R$^{10}$ are identical or different and are a hydrogen atom or an alkyl radical having 1 to 28 carbon atoms, or R$^9$ and R$^{10}$, together with the atoms joining them, can form a ring, at a temperature of –60 to 200° C. under a pressure of 0.5 to 100 bar, in solution, in suspension or in the gas phase, in the presence of a catalyst which consists essentially of a metallocene and an aluminoxane of the formula II

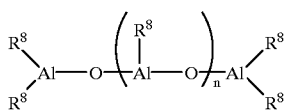
(II)

for the linear type, and/or of the formula III

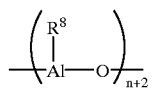
(III)

for the cyclic type, in which, in the formulae II and III, $R^8$ is a $C_1$–$C_6$-alkyl group or a $C_6$–$C_{10}$-aryl group and n is an integer from 2 to 50, wherein the metallocene is a compound of the formula I

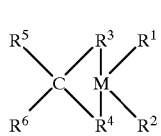
(I)

in which M is a metal of group IVb of the periodic table, $R^1$ and $R^2$ are identical and are a $C_1$–$C_{10}$-alkyl group, or a halogen atom, $R^3$ and $R^4$ are identical and are a mono- or polynuclear hydrocarbon radical which can form a sandwich structure with the transition metal, and $R^5$ and $R^6$ are identical or different and are a hydrogen atom, a $C_1$–$C_{10}$-alkyl group, or a $C_6$–$C_{10}$-aryl group.

2. Process as claimed in claim 1, wherein propylene is polymerized.

3. A process as claimed in claim 1, wherein said M is Ti, Hf or Zr.

4. A process as claimed in claim 1, wherein said $R^1$ and $R^2$ are a $C_1$–$C_3$-alkyl group, or chlorine.

5. A process as claimed in claim 1, wherein said $R^5$ and $R^6$ are identical or different and are a $C_1$–$C_3$-alkyl group, or a $C_6$–$C_8$-aryl group.

6. A process as claimed in claim 1, wherein said temperature ranges from 0° C. to 80° C.

7. The process as claimed in claim 1, wherein propylene is polymerized;

M is Ti, Hf or Zr;

$R^1$ and $R^2$ are a $C_1$–$C_3$-alkyl group or chlorine; and $R^3$ and $R^4$ are identical.

8. The process as claimed in claim 7, wherein said $R^5$ and $R^6$ are identical or different and are a $C_1$–$C_3$-alkyl group, or a $C_6$–$C_8$-aryl group.

9. The process as claimed in claim 8, wherein the temperature range is from 0° C. to 80° C.

10. The process as claimed in claim 9, wherein the metallocene compound is either $R^5R^6C(bis(indenyl))ZrCl_2$ or $R^5R^6C(bis(indenyl))Zr(CH_3)_2$.

11. The process as claimed in claim 10, wherein the metallocene compound is either $Ph_2C(bis(indenyl))ZrCl_2$ or $(CH_3)_2C(bis(indenyl))ZrCl_2$.

12. The process as claimed in claim 11, wherein the metallocene compound is $(CH_3)_2C(bis(indenyl))ZrCl_2$.

13. The process as claimed in claim 1, wherein the metallocene compound is racemic isopropylidene-bis-(1-indenyl)-zirconium dichloride.

14. The process as claimed in claim 1, wherein said olefin is ethylene or propylene.

15. The process as claimed in claim 1, wherein $R^3$ and $R^4$ are an indenyl radical.

16. The process as claimed in claim 1, wherein $R^5$ and $R^6$ are identical or different and are a $C_1$–$C_{10}$-alkyl group or a $C_6$–$C_{10}$-aryl group and said temperature is from 30° C. to 80° C.

17. The process as claimed in claim 15, wherein

M is Hf or Zr;

$R^1$ and $R^2$ are identical and are a $C_1$–$C_3$-alkyl group or a chlorine atom.

18. The process as claimed in claim 17, wherein propylene is polymerized and said temperature ranges from 30° C. to 80° C., and M is Zr and said process takes place without the use or addition of hydrogen gas.

19. The process as claimed in claim 1, wherein the metallocene compound is $R^5R^6C(bis(indenyl))$ $ZrR^1R^2$ wherein $R^1$ and $R^2$ are identical and are halogen or $C_1$–$C_{10}$ alkyl group and $R^5$ and $R^6$ are identical or different and are a $C_1$–$C_3$ alkyl group or $C_6$–$C_8$ aryl group.

20. The process as claimed in claim 19, wherein $R^1$ and $R^2$ are identical and are a $C_1$–$C_3$-alkyl group or chlorine atom and $R^5$ and $R^6$ are identical or different and are a hydrogen atom, a $C_1$–$C_3$-alkyl group or a $C_6$–$C_8$-aryl group.

21. The process as claimed in claim 20, wherein propylene is polymerized and said temperature is from 30° C. to 80° C.

22. A process for the preparation of a polyolefin wax by polymerization or copolymerization of an olefin of the formula $R^9CH=CHR^{10}$, in which $R^9$ and $R^{10}$ are identical or different and are a hydrogen atom or an alkyl radical having 1 to 28 carbon atoms, or $R^9$ and $R^{10}$, together with the atoms joining them, can form a ring, at a temperature of −60 to 200° C. under a pressure of 0.5 to 100 bar, in solution, in suspension or in the gas phase, in the presence of a catalyst which consists essentially of a metallocene and an aluminoxane of the formula II

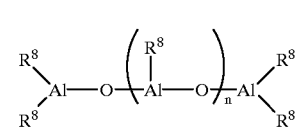
(II)

for the linear type, and/or of the formula III

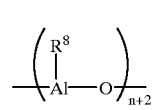
(III)

for the cyclic type, in which, in the formulae II and III, $R^8$ is a $C_1$–$C_6$-alkyl group or a $C_6$–$C_{10}$-aryl group and n is an integer from 2 to 50, wherein the metallocene is a compound of the formula I

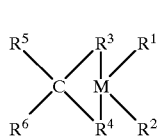
(I)

in which M is a metal of group IVb of the periodic table,
- $R^1$ and $R^2$ are identical and are a $C_1$–$C_{10}$-alkyl group or a halogen atom,
- $R^3$ and $R^4$ are different and $R^3$ is an indenyl radical and $R^4$ is a mono- or polynuclear hydrocarbon radical which can form a sandwich structure with the transition metal, and
- $R^5$ and $R^6$ are identical or different and are a hydrogen atom, a $C_1$–$C_{10}$-alkyl group, or a $C_6$–$C_{10}$-aryl group.

23. The process as claimed in claim 22, wherein M is Hf or Zr; $R^1$ and $R^2$ are a $C_1$–$C_3$-alkyl group or a chlorine atom, $R^4$ is cyclopentadienyl and $R^5$ and $R^6$ are identical or different and are a hydrogen atom, a $C_1$–$C_3$-alkyl group, or a $C_6$–$C_8$-aryl group and said temperature is from 30° C. to 80° C.

24. The process as claimed in claim 23, wherein the polymer produced has a viscosity number being constant throughout the polymerization temperature range and said process takes place without the use or addition of hydrogen gas and said temperature is from 30° C. to 80° C.

25. A process for the preparation of a polyolefin wax by polymerization or copolymerization of an olefin of the formula $R^9CH{=}CHR^{10}$, in which $R^9$ and $R^{10}$ are identical or different and are a hydrogen atom or an alkyl radical having 1 to 28 carbon atoms, or $R^9$ and $R^{10}$, together with the atoms joining them, can form a ring, at a temperature of −60 to 200° C. under a pressure of 0.5 to 100 bar, in solution, in suspension or in the gas phase, in the presence of a catalyst which consists essentially of a metallocene and an aluminoxane of the formula II

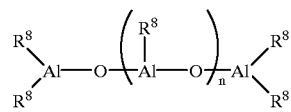
(II)

for the linear type, and/or of the formula III

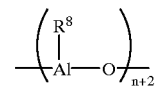
(III)

for the cyclic type, in which, in the formulae II and III, $R^8$ is a $C_1$–$C_6$-alkyl group or a $C_6$–$C_{10}$-aryl group and n is an integer from 2 to 50, wherein the metallocene is a compound of the formula I

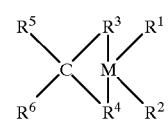
(I)

in which M is a metal of group IVb of the periodic table,
- $R^1$ and $R^2$ are identical and are a $C_1$–$C_{10}$-alkyl group, or a halogen atom,
- $R^3$ and $R^4$ are indenyl radical and
- $R^5$ and $R^6$ are identical or different and are a hydrogen atom, a $C_1$–$C_{10}$-alkyl group or a $C_6$–$C_{10}$-aryl group and
- said process takes place without the use or addition of hydrogen gas.

* * * * *

UNITED STATES PATENT AND TRADEMARK OFFICE
CERTIFICATE OF CORRECTION

PATENT NO.    : 6,063,880
DATED         : May 16, 2000
INVENTOR(S)   : Andreas Winter, Jürgen Rohrmann, Volker Dolle, Martin Antberg and Walter Spaleck Page 1 of 1

It is certified that error appears in the above-identified patent and that said Letters Patent is hereby corrected as shown below:

<u>Claim 1, column 9,</u>
Line 25, formula (I) should be

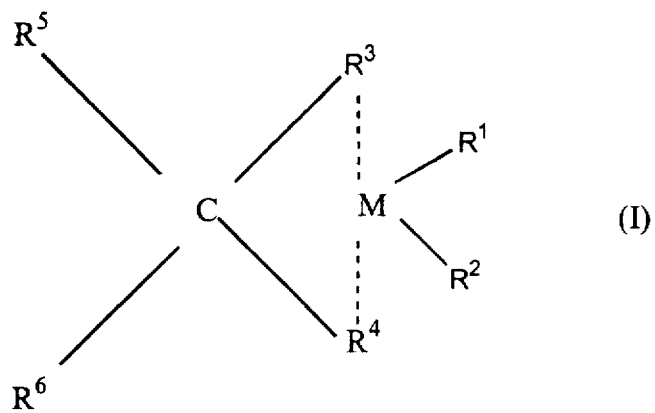

<u>Claim 19, column 10,</u>
Line 27, the word -- a -- should be insert after the word "or".

Signed and Sealed this

Ninth Day of October, 2001

Attest:

NICHOLAS P. GODICI
Attesting Officer    Acting Director of the United States Patent and Trademark Office